United States Patent [19]

Hargrave et al.

[11] Patent Number: 5,602,113

[45] Date of Patent: Feb. 11, 1997

[54] PYRIDOBENZO- AND PYRIDIOTHIENO-DIAZEPINES USEFUL FOR THE TREATMENT OF HIV INFECTION

[75] Inventors: Karl D. Hargrave, Brookfield; Ernest Cullen; John R. Proudfoot, both of Newtown; Karl G. Grozinger, Ridgefield; Kollol Pal, New Milford; Julian Adams, Ridgefield, all of Conn.

[73] Assignee: Boehringer Ingelheim Pharmaceuticals, Inc., Ridgefield, Conn.

[21] Appl. No.: 365,647

[22] Filed: Dec. 29, 1994

Related U.S. Application Data

[63] Continuation of Ser. No. 239,651, May 9, 1994, abandoned, which is a continuation of Ser. No. 91,105, Jul. 13, 1993, abandoned, which is a continuation of Ser. No. 967,609, Oct. 27, 1992, abandoned, which is a continuation of Ser. No. 838,378, Feb. 19, 1992, abandoned, which is a continuation of Ser. No. 652,146, Feb. 7, 1991, abandoned.

[51] Int. Cl.$^6$ .................. A61K 31/55; C07D 471/04; C07D 495/14
[52] U.S. Cl. ............... 514/81; 514/220; 540/542; 540/557
[58] Field of Search ................... 540/542, 557; 514/81, 220

[56] References Cited

U.S. PATENT DOCUMENTS

| | | | |
|---|---|---|---|
| 3,326,900 | 6/1967 | Schmidt | 540/557 |
| 3,917,585 | 11/1975 | Von Bebenburg | 540/557 |
| 4,560,510 | 12/1985 | Lo | 540/557 |
| 5,087,625 | 2/1992 | Hargrave et al. | 514/220 |

OTHER PUBLICATIONS

J. Benditt and J. Cohen, *Science*, vol. 260, May 28, 1993, pp. 1253–1255.

Sandstrom et al., Review Article in *Drugs*, 34, pp. 373–390 (1987).

Yarchoan et al, *AIDS: Modern Concepts and Therapeutic Challanges*, Marcel Dekker Inc. pp. 335–360 (1987).

Hahn et al, "Nucleotide Dimers as Anti-Human Immunodeficiency Virus Agents," in Nucleotide Analogues as Antiviral Agents, Martin ed, Amer. Chem. Soc., pp. 156–159 (1989).

March, *Advanced Organiz Chem.*, 3rd ed. (1985), pp. 527–529.

*Primary Examiner*—Philip I. Datlow
*Attorney, Agent, or Firm*—Robert P. Raymond; Alan R. Stempel; Mary-Ellen M. Devlin

[57] ABSTRACT

Disclosed are novel pyrido[2,3,-b][1,5]benzodiazepines. These compounds are useful in the treatment of AIDS, ARC and related disorders associated with HIV infection.

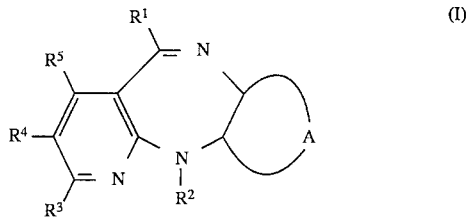

(I)

5 Claims, No Drawings

PYRIDOBENZO- AND PYRIDIOTHIENO-DIAZEPINES USEFUL FOR THE TREATMENT OF HIV INFECTION

This is a continuation of application Ser. No. 239,651, filed May 9, 1994 now abandoned, which is a continuation of application Ser. No. 091,105, filed Jul. 13, 1993, now abandoned, which is a continuation of application Ser. No. 967,609, filed Oct. 27, 1992, now abandoned, which is a continuation of application Ser. No. 838,378, filed Feb. 19, 1992, now abandoned which is a continuation of application Ser. No. 652,146, filed Feb. 7, 1991, now abandoned.

FIELD OF THE INVENTION

The invention relates to novel pyridobenzo-and pyridothieno-diazepines, methods for preparing these compounds, the use of these in the prevention or treatment of HIV infection, and to pharmaceutical compositions containing these compounds.

BACKGROUND OF THE INVENTION

The human disease, Acquired Immune Deficiency Syndrome (AIDS), is caused by the Human Immunodeficiency Virus (HIV), particularly the strain known as HIV-1.

Like other viruses, HIV-1 cannot replicate without comandeering the biosynthetic apparatus of the host cell it infects. It causes this apparatus to produce the structural proteins which make up the viral progeny. These proteins are coded for by the genetic material contained within the infecting virus particle, or virion. Being a retrovirus, however, the genetic material of HIV is RNA, not DNA as in the host cell's genome. Accordingly, the viral RNA must first be converted into DNA, and then integrated into the host cell's genome, in order for the host cell to produce the required viral proteins.

The conversion of the RNA to DNA is accomplished through the use of the enzyme reverse transcriptase (RT), which is included within the infecting virion along with the RNA. Reverse transcriptase has three enzymatic functions; it acts as an RNA-dependent DNA polymerase, as a ribonuclease, and as a DNA polymerase. Acting first as an RNA-dependent DNA polymerase, RT makes a single-stranded DNA copy of the viral RNA. Next, acting as a ribonuclease, RT frees the DNA just produced from the original viral RNA and then destroys the original RNA. Finally, acting as a DNA-dependent DNA polymerase, RT makes a second complementary, DNA strand, using the first DNA strand as a template. The two strands form double-stranded DNA, the form of DNA found in the host cell's genome, which is integrated into the host cell's genome by another enzyme, called an integrase.

Compounds which inhibit the enzymatic functions of HIV-1 reverse transcriptase will inhibit replication of HIV-1 in infected cells. Such compounds are useful in the prevention or treatment of HIV-1 infection in human subjects.

SUMMARY OF THE INVENTION

A first aspect of the invention comprises novel pyridobenzo and pyridothieno-diazepines. These possess inhibitory activity against HIV-1 RT. A second aspect of the invention comprises methods for making these novel compounds. A third aspect of the invention is a method for preventing or treating HIV-1 infection which comprises administering, to a human being exposed to or infected by HIV-1, a prophylactically or therapeutically effective amount of one of the above-mentioned novel compounds. A final aspect of the invention comprises pharmaceutical compositions suitable for the prevention or treatment of HIV-1 infection comprising the above-mentioned compounds.

DETAILED DESCRIPTION OF THE INVENTION

In one of its composition of matter aspects, the invention comprises pyridobenzo and pyridothieno diazephines of the formula I

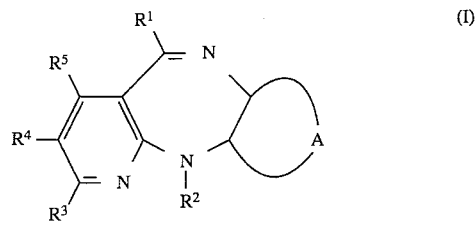

wherein,
A is a fused ring of the formula

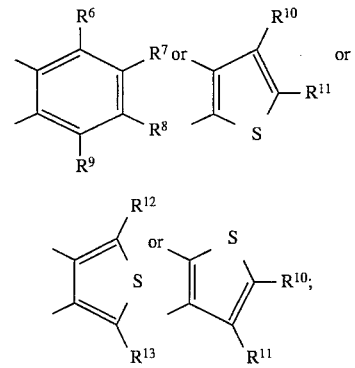

$R^1$ is cyano, chloro, bromo, imadazolyl, phosphetanyl, phospholanyl, or phosphorinanyl, or a group of the formula —$OR^{14}$, —$SR^{14}$, —$SOR^{14}$, —$SO_2R^{14}$, —$NH_2$, —$NHR^{14}$, —$NR^{14}R^{15}$, —$PR^{14}R^{15}$, —$P(OR^{14})(OR^{15})$, —$P(O)(OR^{14})(OR^{15})$, —$PO_3H_2$, —$P(NR^{14}R^{15})(NR^{14}R^{15})$ or —$P(O)(NR^{14}R^{15})(NR^{14}R^{15})$ wherein $R^{14}$ and $R^{15}$ are each independently alkyl of 1 to 4 carbon atoms, which may optionally be substituted by a cyano or alkoxycarbonyl group of 2 to 4 carbon atoms, cyclopropyl or cyclobutyl, or the group —$NR^{14}R^{15}$ is pyrrolidine, piperidine, or morpholine;

$R^2$ is alkyl or fluoroalkyl of 1 to 5 carbon atoms, cycloalkyl of 3 to 5 carbon atoms, alkenyl or alkynyl of 2 to 5 carbon atoms, alkoxyalkyl or alkylthioalkyl of 2 to 4 carbon atoms, alkanoyl of 2 to 4 carbon atoms, hydroxyalkyl of 2 to 5 carbon atoms, arylmethyl (wherein the aryl moiety is phenyl, thienyl or furanyl, which is either unsubstituted or substituted by alkyl or alkoxy of 1 to 3 carbon atoms, hydroxyl, or halogen), phenyl (which is either unsubstituted or substituted by alkyl or alkoxy of 1 to 3 carbon atoms, halogen or hydroxyl) or alkoxy- carbonylmethyl wherein the alkoxy moiety contains 1 to 5 carbon atoms;

$R^3$, $R^4$, and $R^5$ are each independently hydrogen, alkyl of 1 to 3 carbon atoms or chloro, with the proviso that at least one of these substituents is hydrogen; or, one of $R^3$, $R^4$ and $R^5$ is butyl, alkanoyl of 1 to 3 carbon atoms, hydroxyalkyl of 1 to 4 carbon atoms, alkoxycarbonyl of 2 to 3 carbon atoms, alkoxycarbonylalkyl wherein both the alkoxy and alkyl moieties contain 1 to 2 carbon atoms, halogen, trihalomethyl, hydroxyl, alkoxy of 1 to 3 carbon atoms, alkythio of 1 to 3 carbon atoms, alkanoyloxy of 2 to 3 carbon atoms, alkanoylamino of 1 to 3 carbon atoms, aminoalkyl of 1 to 3 carbon atoms, mono- or di-alkylamino or mono- or di-alkylaminocarbonyl wherein each alkyl moiety contains 1 to 2 carbon atoms, carboxyalkyl of 2 to 3 carbon atoms, cyano, nitro, carboxyl, amino, azido or mono- or di-alkylaminoalkyl wherein the alkyl moieties each contain 1 to 2 carbon atoms, and the remaining two substituents are hydrogen or methyl;

$R^6$, $R^7$, $R^8$ and $R^9$ are each hydrogen; or, one of $R^6$, $R^7$, $R^8$ and $R^9$ is alkyl of 1 to 4 carbon atoms, alkanoyl of 1 to 3 carbon atoms, alkoxycarbonyl of 2 to 3 carbon atoms, hydroxyalkyl of 1 to 4 carbon atoms, alkoxycarbonylalkyl wherein both the alkoxy and alkyl moieties contain 1 to 2 carbon atoms, halogen, trihalomethyl, hydroxyl, alkoxy of 1 to 3 carbon atoms, alkylthio of 1 to 3 carbon atoms, alkanoyloxy of 2 to 3 carbon atoms, alkanoylamino of 1 to 3 carbon atoms, aminoalkyl of 1 to 3 carbon atoms, mono- or di-alkylamino or mono- or di-alkylaminocarbonyl wherein each alkyl moiety contains 1 to 2 carbon atoms, carboxyalkyl of 2 to 3 carbon atoms, cyano, nitro, carboxyl, carbamyl, amino, azido or mono- or di-alkylaminoalkyl wherein each alkyl moiety contains 1 to 2 carbon atoms, and the remaining three substituents are hydrogen or two of the remaining three substituents are hydrogen and one is methyl, ethyl or halogen;

$R^{10}$ or $R^{11}$ is hydrogen, alkyl of 1 to 4 carbon atoms, cyano, nitro, halogen or alkanoyl of 1 to 3 carbon atoms, with the remaining substituents being hydrogen, chloro, methyl or ethyl; and, $R^{12}$ and $R^{13}$ are each independently hydrogen, alkyl of 1 to 4 carbon atoms, halogen or nitro, A subgeneric aspect of the invention comprises compounds of the formula Ia

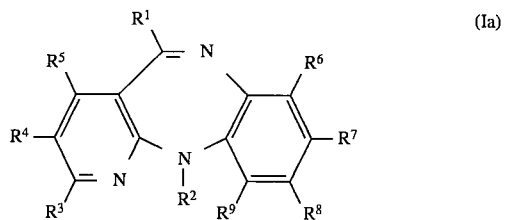

(Ia)

wherein, $R^1$ is cyano, chloro, imidazolyl, or a group of the formula $-OR^{14}$, $-SR^{14}$, $-SOR^{14}$, $-SO_2R^{14}$, $-NH_2$, $-NHR^{14}$, or $-NR^{14}R^{15}$ wherein $R^{14}$ and $R^{15}$ are each independently alkyl of 1 to 4 carbon atoms, which may optionally be substituted by a cyano or alkoxycarbonyl group of 2 to 4 carbon atoms, cyclopropyl or cyclobutyl, or the group $-NR^{14}R^{15}$ is pyrrolidine, piperidine, or morpholine;

$R^2$ is alkyl of 1 to 4 carbon atoms, cycloalkyl of 3 to 4 carbon atoms, alkenylmethyl or alkynylmethyl of 2 to 4 carbon atoms, alkoxyalkyl or alkylthioalkyl of 2 to 4 carbon atoms, alkanoyl of 2 to 3 carbon atoms, hydroxyalkyl of 2 to 4 carbon atoms, arylmethyl (wherein the aryl moiety is phenyl or thienyl, which is either unsubstituted or substituted by methyl, methoxy, hydroxyl or halogen), phenyl (which is either unsubstituted or substituted by methyl, methoxy, hydroxyl or halogen) or alkoxycarbonylmethyl wherein the alkoxy moiety contains 1 to 5 carbon atoms; $R^3$, $R^4$, and $R^5$ are each independently hydrogen or methyl, with the proviso that at least one of these substituents is hydrogen, or $R^5$ is ethyl, propyl or butyl with the other two substituents being hydrogen;

$R^6$ is hydrogen, methyl, ethyl, chloro or trifluoromethyl with the proviso that $R^7$ is hydrogen, methyl or chloro;

$R^7$ is hydrogen, alkyl of 1 to 3 carbon atoms, alkanoyl of 1 to 3 carbon atoms, alkoxycarbonyl of 1 to 3 carbon atoms, hydroxyalkyl of 1 to 3 carbon atoms, alkoxycarbonylalkyl wherein the alkoxy and alkyl moieties each contain 1 to 2 carbon atoms, halogen, trifluoromethyl, hydroxyl, alkoxy or alkylthio of 1 to 2 carbon atoms, acetyloxy, alkanoylamino or aminoalkyl of 1 to 2 carbon atoms, cyano, nitro, amino, or mono- or di-methyl or -ethylamino, with the proviso that $R^8$ is hydrogen, methyl or chloro;

$R^8$ is hydrogen, alkyl of 1 to 3 carbon atoms, alkanoyl of 1 to 3 carbon atoms, alkoxycarbonyl of 1 to 3 carbon atoms, hydroxyalkyl of 1 to 3 carbon atoms, alkoxycarbonylalkyl wherein the alkoxy and alkyl moieties each contain 1 to 3 carbon atoms, halogen, trifluoromethyl, hydroxyl, alkoxy or alkylthio of 1 to 2 carbon atoms, acetyloxy, alkanoylamino or aminoalkyl of 1 to 2 carbon atoms, cyano, nitro, amino, or mono- or di-methyl or -ethylamino with the proviso that $R^7$ is hydrogen, methyl or chloro; and, $R^9$ is hydrogen, methyl, ethyl, chloro or trifluoromethyl with the proviso that $R^8$ is hydrogen, methyl or chloro.

A further subgeneric aspect of the invention compounds of formula Ia, wherein, $R^1$ is cyano, chloro, imidazolyl, or a group of the formula $-OR^{14}$, $-SR^{14}$, $-SOR^{14}$, $-SO_2R^{14}$, $-NH_2$, $-NHR^{14}$, or $-NR^{14}R^{15}$ wherein $R^{14}$ and $R^{15}$ are each independently alkyl of 1 to 4 carbon atoms, which may optionally be substituted by a cyano or alkoxycarbonyl group of 2 to 4 carbon atoms, cyclopropyl or cyclobutyl, or the group $-NR^{14}R^{15}$ is pyrrolidine, piperidine, or morpholine;

$R^2$ is alkyl of 1 to 4 carbon atoms, cycloalkyl of 3 to 4 carbon atoms, alkenyl or alkynyl of 2 to 4 carbon atoms, alkyloxyalkyl or alkylthioalkyl of 2 to 3 carbon atoms, alkanoyl of 2 to 3 carbon atoms, hydroxyalkyl of 2 to 4 carbon atoms, arylmethyl (wherein the aryl moiety is phenyl or thienyl, which is either unsubstituted or substituted by methyl, methoxy or halogen) or alkoxycarbonylmethyl wherein the alkoxy moiety contains 1 to 5 carbon atoms; and, $R^3$ through $R^9$ are as set forth below in Table A.

TABLE A

| | $R^3$ | $R^4$ | $R^5$ | $R^6$ | $R^7$ | $R^8$ | $R^9$ |
|---|---|---|---|---|---|---|---|
| a | H | H | H | H | H | CF_3 | H |
| b | H | H | H | H | Cl | H | H |
| c | H | H | H | H | CH_3 | CH_3 | H |
| d | CH_3 | H | H | H | CH_3 | CH_3 | H |
| e | CH_3 | CH_3 | H | H | CH_3 | CH_3 | H |
| f | H | H | H | CH_3 | CH_3 | H | H |
| g | H | H | H | H | H | Cl | H |
| h | H | H | H | H | H | H | H |
| i | H | H | H | CH_3 | H | H | H |
| j | H | H | H | H | CH_3O_2C— | H | H |
| k | H | H | H | H | C_2H_5O_2C— | H | H |
| l | H | H | H | H | NC— | H | H |
| m | H | H | H | H | CH_3CO— | H | H |
| n | H | H | H | H | H | CH_3O_2C— | H |
| o | H | H | H | H | H | C_2H_5O_2C— | H |
| p | H | H | H | H | H | NC— | H |
| q | H | H | H | H | H | CH_3CO— | H |
| r | H | H | H | H | Cl | Cl | H |
| s | H | H | H | CH_3 | H | CH_3 | H |

A more particular subgeneric aspect of the invention comprises compounds of formula Ia wherein, $R^1$ is cyano, imidazolyl, or a group of the formula $-OR^{14}$, $-SR^{14}$, $-SOR^{14}$, $-SO_2R^{14}$, $-NH_2$, $-NHR^{14}$, or $-NR^{14}R^{15}$ wherein $R^{14}$ and $R^{15}$ are each independently alkyl of 1 to 4 carbon atoms, which may optionally be substituted by a cyano or alkoxycarbonyl group of 2 to 4 carbon atoms, cyclopropyl or cyclobutyl, or the group —NR$^{14}$R$^{15}$ is pyrrolidine, piperidine, or morpholine;

R$^2$ is alkyl of 2 to 3 carbon atoms, cyclopropyl or allyl;

R$^3$ through R$^9$ are each hydrogen; or,

R$^3$R$^4$, R$^5$, R$^6$, and R$^9$ are each hydrogen; and,

R$^7$ and R$^8$ are each independently hydrogen, methyl, or chloro, with the proviso that at least one of R$^7$ and R$^8$ is methyl or chloro.

Synthesis of Compounds of Formula I and their Salts

The compounds of Formula I and their salts can be prepared by known methods or obvious modifications thereof. Methods A–I, described below, are illustrative of the methods of preparing the compounds.

Method A (nitrile)

Compounds of the formula I, wherein R$^2$ through R$^{13}$ are as defined above and R$^1$ is cyano, can be obtained by treating a trifluoromethanesulfonate of formula I, wherein R$^2$ through R$^{13}$ are as defined above and R$^1$ is trifluoromethanesulfonate, with cyanide ion. Convenient sources of cyanide ion include, for example, tetraethylammonium cyanide, diethylaluminum cyanide, potassium cyanide, or sodium cyanide. The reaction is preferably carried out in an inert solvent, for example, methylene chloride, chloroform, dimethylformamide, dimethylsulfoxide, diethylether, or tetrahydrofuran, at a temperature between 0° C. and the boiling point of the reaction mixture.

Method B (halide)

Compounds of the formula I, wherein R$^2$ through R$^{13}$, are as defined above and R$^1$ is chloro or bromo, can be obtained by treating a lactam of the formula II,

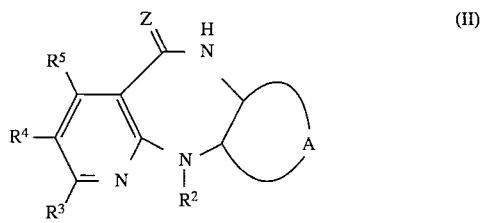

wherein A and R$^2$ through R$^{13}$ are as defined above and Z is oxygen, with a halogenating agent in an inert solvent. Chlorinating agents which may be used include, for example, phosphorus pentachloride, phosphorus oxychloride, and sulfuryl chloride. Brominating agents which may be used include, for example, phosphorus pentabromide or phosphorus oxybromide. The reaction is conveniently carried out at temperatures of between 0° C. and the boiling point of the reaction mixture, preferably at temperatures above ambient temperature, and inert solvents which may be used include, for example, toluene, xylene, dichlorethane, or trichlorobenzene.

Method C (alkoxide)

Compounds of the formula I, wherein R$^1$ is a group of the formula —OR$^{14}$, and R$^2$ through R$^{13}$ are as defined above, may be obtained by reacting a compound of the formula I, wherein R$^1$ is cyano and R$^2$ through R$^{13}$ are as defined above, with an alcohol of formula R$^{14}$OH. The condensation is conveniently carried out in the presence of a base including, but not limited to, an alkali metal or alkaline earth metal hydroxide, such as lithium hydroxide, barium hydroxide, sodium hydroxide or potassium hydroxide, or an alkali metal alkoxide, such as sodium methoxide or potassium tert-butoxide, and using the alcohol as solvent, at a temperature between −20° C. and +50° C. It is preferable that the alkali metal alkoxide utilized be derived from the alcohol which is used as solvent.

Method D (alkylthio)

Compounds of the formula I, wherein R$^1$ is a group of the formula —SR$^{14}$, and R$^2$ through R$^{14}$ are as defined above, may be obtained by converting a compound of the formula II, wherein R$^2$ through R$^{13}$ are as defined above and Z is sulfur, into the corresponding 5-alkali or alkaline earth metal compound and subsequently reacting the alkali metal compound with a compound of the formula III

R$^{14}$X                        (III)

wherein R$^{14}$ has the same meanings as defined above and X is the radical of a reactive ester, a halogen atom, or the group OSO$_2$R wherein R is methyl, ethyl or an aromatic group.

The conversion of a compound of formula II into the corresponding alkali metal or alkaline earth metal compound may be effected by reacting a compound of formula II with an alkali metal or alkaline earth metal hydroxide, such as lithium hydroxide, barium hydroxide, sodium hydroxide or potassium hydroxide, with an alkali metal alkoxide, such as sodium methoxide or potassium tert-butoxide, with an alkali metal amide, such as sodium amide or potassium amide, or with an alkali metal hydride such as sodium hydride or potassium hydride. The reaction is preferably carried out at temperatures between −78° C. and +50° C., and in the presence of a suitable organic solvent. Inert organic solvents, such as dimethylformamide, dimethylsulfoxide, tetrahydrofuran, glycoldimethyl ether, toluene, pyridine, or methylene chloride are preferred. For conversion of the alkali or alkaline earth metal-substituted compound thus obtained into a compound of formula I, the solution or suspension of the alkali or alkaline earth metal compound is reacted directly, i.e. without isolation, with a compound of formula III. Substitution takes place at the sulfur atom in the 6-position of the dipyridodiazepinone, even if R$^2$ in the starting material of formula II is a hydrogen atom, provided that one equivalent of base and one equivalent of a compound of formula III are used.

It will be obvious to those skilled in the art that the presence of nucleophilic substituents in the compounds of formula II may require the use of an intermediate of formula II having substituents which are, other than the 11-position nitrogen, not nucleophilic but which can be derivatized to yield the required group. For example, amino or monoalkylamino substituents at any of R$^3$ through R$^{13}$ may be obtained by alkylating or acylating an intermediate of formula II having a nitro group at any of R$^3$ through R$^{13}$, and subsequently reducing the nitro group, and alkylating, if appropriate, to yield the final product.

Method E (sulfoxide)

Compounds of the formula I, wherein R$^1$ is a group of the formula —SOR$^{14}$, and R$^2$ through R$^{14}$ are as defined above, may be obtained by oxidizing a compound of the formula I, wherein R$^1$ is a group of the formula —SR$^{14}$ and R$^2$ through R$^{14}$ are as defined above. Oxidizing agents which may be used include peroxides such as 30% hydrogen peroxide, peracids such as m-chloroperbenzoic acid or trifluoroperacetic acid, sodium periodate, sodium perborate, or t-butyl hypochlorite. The reaction is carried out in inert solvents such as methylene chloride, dichlorethane, acetic acid, acetone, and toluene at temperatures generally from −78° C. to 25° C.

Method F (sulfone)

Compounds of the formula I, wherein R$^1$ is a group of the formula —SO$_2$R$^{14}$, and R$^2$ through R$^{14}$ are as defined above, may be obtained by oxidizing a compound of the formula I, wherein R$^1$ is a group of the formula —SR$^{14}$ or —SOR$^{14}$, and R$^2$ through R$^{14}$ are as defined above. Oxidizing agents which may be used include peroxides such as 30% hydrogen peroxide, potassium permanganate, potassium hydrogen persulfate, peracids such as m-chloroperbenzoic acid or trifluoroperacetic acid, sodium periodate, sodium perborate, or t-butyl hypochlorite. The reaction can be carried out in inert solvents such as methylene chloride, dichloroethane, acetic acid, acetone, and toluene at temperatures generally from −78° C. to 25° C. Generally, these reactions are performed analogously to those for for the preparation of the corresponding sufoxides, except that an additional equivalent of oxidizing agent is utilized, and the reaction may be carried out at higher temperatures.

Method G (amine)

Compounds of formula I, wherein $R^1$ is a group of the formula —$NH_2$, —$NHR^{14}$, —$NR^{14}R^{15}$, or imidazolyl, and $R^2$ through $R^{13}$ are as defined above, may be obtained by reaction of a compound of formula I, wherein $R^1$ is trifluoromethanesulfonate, with a molar excess of ammonia or an amine of the formula $H_2NR^{14}$, $HNR^{14}R^{15}$, or imidazole. The condensation is generally carried out in an inert solvent such as methylene chloride, dioxane, dimethylformamide, dimethylsulfoxide, tetrahydrofuran, or toluene, at temperatures between −20° C. up to the boiling point of the solvent.

Method H (phosphorous compounds)

Compounds of formula I, wherein $R^1$ is a group of the formula —$PR^{14}R^{15}$, —$P(OR^{14})(OR^{15})$, —$P(O)(OR^{14})(OR^{15})$, —$P(NR^{14}R^{15})(NR^{14}R^{15})$, —$P(O)(NR^{14}R^{15})(NR^{14}R^{15})$, P-phosphentanyl, P-phospholanyl, or P-phosphorinanyl, and $R^2$ through $R^{15}$ are as defined above, may be obtained by transmetallation of a compound of formula I, wherein $R^1$ is halogen with a bulky alkyllithium reagent such as t-butyllithium. The reaction is generally carried out in inert solvents such as tetrahydrofuran, diethyl ether, 1,4-dioxane, and glycoldimethyl ether. The lithio derivative thus formed is then reacted with an appropriate halophosphorous compound of the formula $XPR^{14}R^{15}$, $XP(OR^{14})(OR^{15})$, $XP(O)(OR^{14})(OR^{15})$, $XP(NR^{14}R^{15})$, $XP(O)(NR^{14}R^{15})(NR^{14}R^{15})$, P-halophosphetanyl, P-halophospholanyl, or P-halophosphorinanyl, wherein X is halogen. These reactions are generally carried out in a single reaction vessel at temperatures between −78° C. and room temperature.

Method I (phosphonic acids)

Compounds of formula I, wherein $R^1$ is a group of the formula —$PO_3H_2$ and $R^2$ through $R^{13}$ are as defined above, may be obtained by hydrolysis of a compound of formula I, wherein $R^1$ is a group of formula —$P(OR^{14})(OR^{15})$, wherein $R^{14}$ and $R^{15}$ are as defined above. The hydrolysis is generally carried out in an aqueous solution containing an alkaline earth metal hydroxide, such as lithium hydroxide, barium hydroxide, sodium hydroxide or potassium hydroxide, optionally in the presence of an inert organic solvent such as methanol or ethanol, at temperatures between 0° C. and the boiling point of the reaction mixture.

Starting Materials for Methods A through I

The preparation of compounds of formula I wherein $R^1$ is trifluoromethanesulfonate and $R^2$ through $R^{13}$ are as defined above, and compounds of formula II wherein $R^2$ through $R^{13}$ are as defined above, can be obtained by procedures described in U.S. patent application Ser. No. 08/291,634 filed Aug. 17, 1994.

Those skilled in the art will realize that it will at times be more convenient to make certain compounds of formula I by derivatization of other compounds of formula I, rather than by making them directly, using one of the above-described Methods A–G. Such derivatizations will employ known reaction techniques. As non-limiting examples, a nitro group can be reduced to yield an amine; a methoxy group can converted to hydroxy by standard demethylation procedures and hydroxy can, in appropriate settings, be in turn replaced with amine via the trifluoromethanesulfonyloxy derivative; an amine can be acylated to yield an alkanoylamine or can be alkylated to yield the mono- or dialkylamine; a halogen can be replaced, in appropriate settings, by an amine; and a protecting group can be removed.

Formation of Salts and Other Derivatives

Compounds of formula I may, if desired, be converted into their non-toxic, pharmaceutically acceptable addition salts by conventional methods; for example, by dissolving a compound of formula I in a suitable solvent and treating the solution with one or more molar equivalents of the desired acid or base, as appropriate. The invention also comprises such salts.

Examples of inorganic and organic acids which may form nontoxic, pharmaceutically acceptable acid addition salts with a compound of the formula I are the following: hydrochloric acid, hydrobromic acid, sulfuric acid, phosphoric acid, nitric acid, methanesulfonic acid, tartaric acid, fumaric acid, acetic acid, and the like. Examples of inorganic and organic bases which may form nontoxic, pharmaceutically acceptable basic addition salts with a compound of the formula I are the following: Sodium hydroxide, potassium hydroxide, magnesium hydroxide, ammonia, tromethamine, and the like. Compounds of formula I may form addition salts with one molar equivalent of the acid or base, as appropriate.

Biological Properties

The above-described compounds of Formula I, and their salts, possess inhibitory activity against HIV-1 reverse transcriptase. When administered in suitable dosage forms, they are useful in the prevention or treatment of AIDS, ARC and related disorders associated with HIV infection. Another aspect of the invention, therefore, is a method for preventing or treating HIV-1 infection which comprises administering to a human being, exposed to or infected by HIV-1, a prophylactically or therapeutically effective amount of a novel compound of Formula I, as described above.

The above described compounds of formula I may be administered in single or divided doses by the oral, parenteral or topical routes. A suitable oral dosage for such compounds would be in the range of about 5 to 1000 mg per day. In parenteral formulations, a suitable dosage unit may contain from about 0.1 to 250 mg of said compounds, whereas for topical administration, formulations containing about 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When these compounds are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkyleneglycols, petroleum jelly and the like.

The pharmaceutical preparations can be prepared in a conventional manner and finished dosage forms can be solid dosage forms, for example, tablets, dragees, capsules, and the like, or liquid dosage forms, for example, solutions, suspensions, emulsions and the like. Further, the pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, these compounds can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The above described compounds can also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chlorobutanol or phenylethyl alcohol.

Additionally, these compounds can be administered by suppository.

Utilizing the Reverse Transcriptase (RT) Assay described below, the compounds of Examples 1 and 2 were tested for their ability to inhibit the RNA-dependent DNA polymerase activity of HIV-1 RT. At a dose of 10 µg/ml, the compound of Example 1 inhibited the enzyme by 59%, and the compound of Example 2 inhibited the enzyme by 82%.

REVERSE TRANSCRIPTASE (RT) ASSAY

Assay Theory:

Among the enzymes for which Human Immunodeficiency Virus (HIV-1) encodes is a reverse transcriptase (1), so-named because it transcribes a DNA copy from an RNA template. This activity can be quantitatively measured in a cell-free enzyme assay, which has been previously described (2), and is based upon the observation that reverse transcriptase is able to use a synthetic template [poly r(C) primed with oligo d(G)] to transcribe a radio-labelled, acid-precipitable DNA strand utilizing $^3$H-dGTP as a substrate.

Materials:

a) Preparation of the enzyme

Reverse transcriptase enzyme from the LAV strain of Human Immunodeficiency Virus (HIV-1) (1) was isolated from the bacterial strain JM109 (3) expressing the DNA clone pBRTprtl+(2) which is under the control of the lac promotor in the expression vector pIBI21 (4). An overnight culture grown in 2XYT medium (37° C., 225 rpm) (5) supplemented with 100 µg/ml ampicillin for positive selection is inoculated at a 1:40 dilution into M9 medium supplemented with 10 µg/ml thiamine, 0.5% casamino acids, and 50 µg/ml ampicillin (5). The culture is incubated (37° C., 225 rpm) until it reaches an OD540 of 0.3–0.4. At that time the repressor inhibitor IPTG (isopropyl β-D-thiogalactopyranoside) is added to 0.5 mM, and the mixture is incubated for 2 additional hours. Bacteria are pelleted, resuspended in a 50 mM Tris, 0.6 mM EDTA, 0.375M NaCl buffer and digested by the addition of lysozyme (1 mg/ml) for 30 minutes on ice. The cells are lysed by the addition of 0.2% NP-40 and brought to 1M NaCl.

After removal of the insoluble debris by centrifugation, the protein is precipitated by the addition of 3 volumes of saturated aqueous ammonium sulfate. The enzyme is pelleted, resuspended in RT buffer (50 mM Tris pH 7.5, 1 mM EDTA, 5 mM DTT, 0.1% NP-40, 0.1M NaCl, and 50% glycerol), and stored at −70° C. for further use.

| Stock Reagent | 2X Mix Concentration |
|---|---|
| 1M Tris pH 7.4 | 100 mM |
| 1M Dithiothrietol | 40 mM |
| 1M NaCl | 120 mM |
| 1% Nonidet P-40 | 0.1% |
| 1M MgCl | 4 mM |
| [poly r(C)/oligo d(G)](5:1) | 2 µg/ml |
| $^3$H-dGTP (81 µM) | 0.6 µM |

Assay Procedure:

The 2X concentrated stock reaction mixture is aliquoted and stored at −20° C. The mixture is stable and thawed for use in each assay. This enzyme assay has been adapted to a 96 well microtiter plate system, and has been previously described (6). Tris buffer (50 mM, pH 7.4), vehicle (solvent diluted to match the compound dilution), or compounds in vehicle are dispensed into 96-well microtiter plates (10 µl/well; 3 wells/compound). The HIV-1 RT enzyme is thawed, diluted in 50 mM Tris pH 7.4 so that fifteen µl of diluted enzyme contain 0.001 Unit (one unit is that amount of enzyme to transform 1 micromole of substrate per minute at 25° C.), and fifteen µl are dispensed per well. Twenty µl of 0.12–0.5M EDTA are added to the first three wells of the microtiter plate. EDTA chelates the $Mg^{++}$ present and prevents reverse transcription. This group serves as background polymerization which is subtracted from all other groups. Twenty-five ul of the 2X reaction mixture are added to all wells and the assay is allowed to incubate at room temperature for 60 minutes. The assay is terminated by precipitating the DNA in each well with 50 µl of 10% trichloracetic acid (TCA) (10% w/v) in sodium pyrophosphate (1% w/v). The microtiter plate is incubated for 15 minutes at 4° C. and the precipitate is fixed onto #30 glass fiber paper (Schleicher & Schuell) using a Skatron semi-automatic harvester. The filters are then washed with additional TCA (5%) containing sodium pyrophosphate (1%), rinsed with aqueous ethanol (70%), dried, and transferred to scintillation vials (6). Each vial receives 2 mls of scintillation cocktail and is counted in a Beckman beta counter.

The calculation for percent inhibition is as follows:

% inhibition =

$$\frac{CPM \text{ Mean Test Value} - CPM \text{ Mean Control Value} \times 100}{CPM \text{ Mean Control Value}}$$

References:

1. benn, S., et al., *Science* 230:949, 1985.

2. Farmerie, W. G. et. al., *Science* 236:305, 1987.

3. Yanisch-Perron, C., Viera, J., and Messing, J., *Gene* 33:103, 1985.

4. International Biotechnologies, Inc., New Haven, Conn. 06535.

5. Maniatis, T, Fritsch, E. F., and J. Sambrook, eds. *Molecular Cloning: A Laboratory Manual,* Cold Spring Harbor Laboratory, 1982.

6. Spira, T., et al. *J. Clinical Microbiology,* 25:97, 1987.

The following examples further illustrate the present invention and will enable others skilled in the art to understand the invention more completely. It should be understood, however, that the invention is not limited to the particulars given in the examples.

EXAMPLE 1

5-Ethoxy-7-methyl-11H-pyrido[2,3-b][1,5]benzodiazepine

Sodium hydride (80% oil dispersion, 0.13 g, 5.5 mmol) was added at room temperature to a suspension of 6,11-dihydro-7-methyl-5H-pyrido[2,3-b][1,5]benzodiazepin-5-one (1.12 g, 5.0 mmol) in DMF (20 mL) under argon. The reaction mixture was heated at 60° C. for 1 h and then was cooled in an ice-bath before the addition of ethyl iodide (0.86 g, 5.5 mmol). Stirring was continued at room temperature overnight, followed by warming to 60° C. for 1 h. The solution was concentrated in vacuo to near dryness, the residue was poured over ice-water, and the resulting solid was collected, washed with water, and dried. Purification by chromatography (elution with 1% MeOH/CH$_2$Cl$_2$) afforded 0.23 g (18%) of the title compound, which crystallized as yellow needles from petroleum ether (30°–60° C.): m.p. 135°–136° C.

EXAMPLE 2

5-Methoxy-11-methyl-11H-pyrido[2,3-b][1,5]benzodiazepine

The title compound, a semi-crystalline substance, was synthesized in a manner analogous to that described in Example 1.

EXAMPLE A

Capsules or Tablets

| A-1 Ingredients | Quantity | A-2 Ingredients | Quantity |
| --- | --- | --- | --- |
| Compound of Ex. 2 | 250 mg | Compound of Ex. 2 | 50 mg |
| Starch | 160 mg | Dicalcium Phosphate | 160 mg |
| Microcrys. Cellulose | 90 mg | Microcrys. Cellulose | 90 mg |
| Sodium Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of Example 2 is blended into a powder mixture with the premixed excipient materials as identified above with the exception of the lubricant. The lubricant is then blended in and the resulting blend compressed into tablets or filled into hard gelatin capsules.

EXAMPLE B

Parenteral Solutions

| Ingredients | Quantity |
| --- | --- |
| Compound of Example 2 | 500 mg |
| Tartaric acid | 1.5 g |
| Benzyl Alcohol | 0.1% by weight |
| Water for injection | q.s. to 100 ml |

The excipient materials are mixed with the water and thereafter the compound of Example 2 is added. Mixing is continued until the solution is clear. The pH of this solution is adjusted to 3.0 and is then filtered into the appropriate vials or ampoules and sterilized by autoclaving.

EXAMPLE C

Nasal Solutions

| Ingredients | Quantity |
| --- | --- |
| Compound of Example 2 | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 ml |

The excipient materials are mixed with the water and thereafter the compound of Example 2 is added and mixing is continued until the solution is clear. The pH of this solution is adjusted to 4.0 and is then filtered into the appropriate vials or ampoules.

We claim:

1. A compound of the formula I

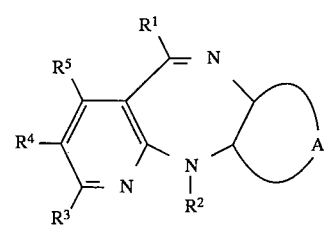

wherein,

A is a fused ring of the formula

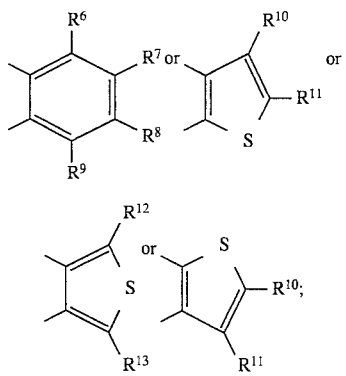

R¹ is cyano, chloro, bromo, imidazolyl, phosphetanyl, phospholanyl, or phosphorinanyl, or a group of the formula —OR¹⁴, —SR¹⁴, —SOR¹⁴, —SO₂R¹⁴, —NH₂, —NHR¹⁴, —NR¹⁴R¹⁵, —PR¹⁴R¹⁵, —P(OR¹⁴)(OR¹⁵), —P(O)(OR¹⁴)(OR¹⁵), —PO₃H₂, —P(NR¹⁴R¹⁵)(NR¹⁴R¹⁵) or —P(O)(NR¹⁴R¹⁵) wherein R¹⁴ and R¹⁵ are each independently alkyl of 1 to 4 carbon atoms, which may optionally be substituted by a cyano or alkoxycarbonyl group of 2 to 4 carbon atoms, cyclopropyl or cyclobutyl, or the group —NR¹⁴R¹⁵ is pyrrolidine, piperidine, or morpholine;

R² is alkyl or fluoroalkyl of 1 to 5 carbon atoms, cycloalkyl of 3 to 5 carbon atoms, alkenyl or alkynyl of 2 to 5 carbon atoms, alkoxyalkyl or alkylthioalkyl of 2 to 4 carbon atoms, alkanoyl of 2 to 4 carbon atoms, hydroxyalkyl of 2 to 5 carbon atoms, arylmethyl (wherein the aryl moiety is phenyl, thienyl or furanyl, which is either unsubstituted or substituted by alkyl or alkoxy of 1 to 3 carbon atoms, hydroxyl, or halogen), phenyl (which is either unsubstituted or substituted by alkyl or alkoxy of 1 to 3 carbon atoms, halogen or hydroxyl) or alkoxy- carbonylmethyl wherein the alkoxy moiety contains 1 to 5 carbon atoms;

R³, R⁴, and R⁵ are each independently hydrogen, alkyl of 1 to 3 carbon atoms or chloro, with the proviso that at least one of these substituents is hydrogen; or, one of R³, R⁴ and R⁵ is butyl, alkanoyl of 1 to 3 carbon atoms, hydroxyalkyl of 1 to 4 carbon atoms, alkoxycarbonyl of 2 to 3 carbon atoms, alkoxycarbonylalkyl wherein both the alkoxy and alkyl moieties contain 1 to 2 carbon atoms, halogen, trihalomethyl, hydroxyl, alkoxy of 1 to 3 carbon atoms, alkythio of 1 to 3 carbon atoms, alkanoyloxy of 2 to 3 carbon atoms, alkanoylamino of 1 to 3 carbon atoms, aminoalkyl of 1 to 3 carbon atoms, mono- or di-alkylamino or mono- or di-alkylaminocarbonyl wherein each alkyl moiety contains 1 to 2 carbon atoms, carboxyalkyl of 2 to 3 carbon atoms, cyano, nitro, carboxyl, carbamyl, amino, azido or mono- or di-alkylaminoalkyl wherein the alkyl moieties each contain 1 to 2 carbon atoms, and the remaining two substituents are hydrogen or methyl;

R⁶, R⁷, R⁸ and R⁹ are each hydrogen; or, one of R⁶, R⁷, R⁸ and R⁹ is alkyl of 1 to 4 carbon atoms, alkanoyl of 1 to 3 carbon atoms, alkoxycarbonyl of 2 to 3 carbon atoms, hydroxyalkyl of 1 to 4 carbon atoms, alkoxycarbonylalkyl wherein both the alkoxy and alkyl moieties contain 1 to 2 carbon atoms, halogen, trihalomethyl, hydroxyl, alkoxy of 1 to 3 carbon atoms, alkylthio of 1 to 3 carbon atoms, alkanoyloxy of 2 to 3 carbon atoms, alkanoylamino of 1 to 3 carbon atoms, aminoalkyl of 1 to 3 carbon atoms, mono- or di-alkylamino or mono- di-alkylaminocarbonyl wherein each alkyl moiety contains 1 to 2 carbon atoms, carboxyalkyl of 2 to 3 carbon atoms, cyano, nitro, carboxyl, carbamyl, amino, azido or mono- or di-alkylaminoalkyl wherein each alkyl moiety contains 1 to 2 carbon atoms, and the remaining three substituents are hydrogen or two of the remaining three substituents are hydrogen and one is methyl, ethyl or halogen;

R¹⁰ or R¹¹ is hydrogen, alkyl of 1 to 4 carbon atoms, cyano, nitro, halogen or alkanoyl of 1 to 3 carbon atoms, with the remaining substituent being hydrogen, chloro, methyl or ethyl; and, R¹² and R¹³ are each independently hydrogen, alkyl of 1 to 4 carbon atoms, halogen or nitro;

or a pharmaceutically acceptable addition salt thereof.

2. A compound of the formula Ia

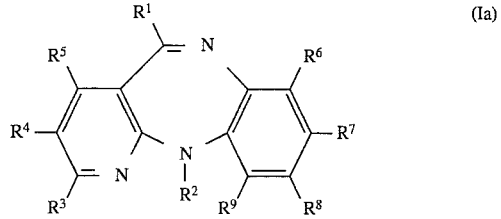

(Ia)

wherein,

R¹ is cyano, chloro, imidazolyl, or a group of the formula —OR¹⁴, —SR¹⁴, —SOR¹⁴, —SO₂R¹⁴, —NH₂, —NHR¹⁴, or —NR¹⁴R¹⁵ wherein R¹⁴ and R¹⁵ are each independently alkyl of 1 to 4 carbon atoms, which may optionally be substituted by a cyano or alkoxycarbonyl group of 2 to 4 carbon atoms, cyclopropyl or cyclobutyl, or the group —NR¹⁴R¹⁵ is pyrrolidine, piperidine, or morpholine;

R² is alkyl of 1 to 4 carbon atoms, cycloalkyl of 3 to 4 carbon atoms, alkenyl or alkynyl of 2 to 4 carbon atoms, alkyloxyalkyl or alkylthioalkyl of 2 to 3 carbon atoms, alkanoyl of 2 to 3 carbon atoms, hydroxyalkyl of 2 to 4 carbon atoms, arylmethyl (wherein the aryl moiety is phenyl or thienyl, which is either unsubstituted or substituted by methyl, methoxy or halogen) or alkoxycarbonylmethyl wherein the alkoxy moiety contains 1 to 5 carbon atoms; and, R³ through R⁹ are as set forth below in Table A

TABLE A

|   | R³ | R⁴ | R⁵ | R⁶ | R⁷ | R⁸ | R⁹ |
|---|----|----|----|----|----|----|-----|
| a | H | H | H | H | H | CF₃ | H |
| b | H | H | H | H | Cl | H | H |
| c | H | H | H | H | CH₃ | CH₃ | H |
| d | CH₃ | H | H | H | CH₃ | CH₃ | H |
| e | CH₃ | CH₃ | H | H | CH₃ | CH₃ | H |
| f | H | H | H | CH₃ | CH₃ | H | H |
| g | H | H | H | H | H | Cl | H |
| h | H | H | H | H | H | H | H |
| i | H | H | H | CH₃ | H | H | H |
| j | H | H | H | H | CH₃O₂C— | H | H |
| k | H | H | H | H | C₂H₅O₂C— | H | H |
| l | H | H | H | H | NC— | H | H |
| m | H | H | H | H | CH₃CO— | H | H |
| n | H | H | H | H | H | CH₃O₂C— | H |
| o | H | H | H | H | H | C₂H₅O₂C— | H |
| p | H | H | H | H | H | NC— | H |
| q | H | H | H | H | H | CH₃CO— | H |
| r | H | H | H | H | Cl | Cl | H |
| s | H | H | H | CH₃ | H | CH₃ | H | or a pharmaceutically acceptable addition salt thereof.

3. A compound of the formula Ia:

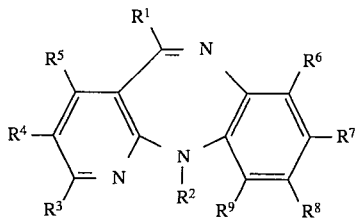

wherein, $R^1$ is cyano, chloro, imidazolyl, or a group of the formula —$OR^{14}$, —$SR^{14}$, —$SOR^{14}$, —$SO_2R^{14}$, —$NH_2$, —$NHR^{14}$, or —$NR^{14}R^{15}$ wherein $R^{14}$ and $R^{15}$ are each independently alkyl of 1 to 4 carbon atoms, which may optionally be substituted by a cyano or alkoxycarbonyl group of 2 to 4 carbon atoms, cyclopropyl or cyclobutyl, or the group —$NR^{14}R^{15}$ is pyrrolidine, piperidine, or morpholine;

$R^2$ is alkyl of 2 to 3 carbon atoms, cyclopropyl or allyl;

$R^3$ through $R^9$ are each hydrogen; or, $R^3$, $R^4$, $R^5$, $R^6$, and $R^9$ are each hydrogen; and, $R^7$ and $R^8$ are each independently hydrogen, methyl, or chloro, with the proviso that at least one of $R^7$ and $R^8$ is methyl or chloro;

or a pharmaceutically acceptable addition salt thereof.

4. A method for treating infection by HIV-1 which comprises administering to a human exposed to or infected by HIV-1 a therapeutically effective amount of a compound according to claims 1, 2, or 3.

5. A pharmaceutical composition suitable for the treatment of HIV-1 infection comprising a therapeutically effective amount of a compound according to claims 1, 2 or 3 and a pharmaceutically acceptable carrier.

* * * * *